(12) United States Patent
Mathew

(10) Patent No.: US 11,464,710 B2
(45) Date of Patent: Oct. 11, 2022

(54) AUTOMATED AND SECURE METHODS FOR DISPENSING MEDICATION

(71) Applicant: TUPELOLIFE SERVICES, LLC, Dallas, TX (US)

(72) Inventor: Melvin Mathew, Dubai (AE)

(73) Assignee: TUPELOLIFE SERVICES, LLC, Dallas, TX (US)

( * ) Notice: Subject to any disclaimer, the term of this patent is extended or adjusted under 35 U.S.C. 154(b) by 0 days.

(21) Appl. No.: 16/647,410

(22) PCT Filed: Sep. 12, 2018

(86) PCT No.: PCT/US2018/050722
§ 371 (c)(1),
(2) Date: Mar. 13, 2020

(87) PCT Pub. No.: WO2019/055545
PCT Pub. Date: Mar. 21, 2019

(65) Prior Publication Data
US 2020/0253828 A1 Aug. 13, 2020

Related U.S. Application Data

(60) Provisional application No. 62/558,630, filed on Sep. 14, 2017.

(51) Int. Cl.
*G16H 20/13* (2018.01)
*A61J 7/04* (2006.01)
(Continued)

(52) U.S. Cl.
CPC ........... *A61J 7/0445* (2015.05); *A61J 7/0076* (2013.01); *A61J 7/0436* (2015.05); *G16H 10/60* (2018.01);
(Continued)

(58) Field of Classification Search
CPC ..... A61J 2200/70; G16H 20/13; G16H 40/67; G07F 17/0092
See application file for complete search history.

(56) References Cited

U.S. PATENT DOCUMENTS 5,084,828 A * 1/1992 Kaufman ............... A61J 7/0084
700/242
6,471,087 B1 * 10/2002 Shusterman ........... G16H 20/13
221/2

(Continued)

FOREIGN PATENT DOCUMENTS

WO 2017/062986 A1 4/2017

OTHER PUBLICATIONS

International Search Report and Written Opinion dated Jan. 2, 2019 for International Application No. PCT/US2018/050722, 26 pages.
(Continued)

*Primary Examiner* — Timothy R Waggoner
(74) *Attorney, Agent, or Firm* — Kilpatrick Townsend & Stockton LLP

(57) ABSTRACT

A point of care device for securely dispensing medication includes an enclosure sized to contain medication containers, a holding element accessible from outside the enclosure to receive medication containers from the enclosure, a dispenser to dispense medication from the enclosure to the holding element, and a securable panel configured to provide access to the enclosure for retrieval or replenishment of the medication containers within the enclosure, and a computing device operable to control the dispenser to dispense medication to the holding element based on various conditions. Specifically, the point of care device can be configured to dispense medication based on detecting that an authorized user is accessing the device, based on a timer in conjunction with known medication regimen, or based on patient or physician demand, or based on biometric information concerning the user.

19 Claims, 9 Drawing Sheets

(51) Int. Cl.
*G16H 40/67* (2018.01)
*G16H 10/60* (2018.01)
*G16H 50/20* (2018.01)
*G16H 80/00* (2018.01)
*A61J 7/00* (2006.01)

(52) U.S. Cl.
CPC ............. *G16H 20/13* (2018.01); *G16H 40/67* (2018.01); *G16H 50/20* (2018.01); *G16H 80/00* (2018.01); *A61J 2200/70* (2013.01)

(56) References Cited

U.S. PATENT DOCUMENTS

| | | | |
|---|---|---|---|
| 8,196,774 | B1 | 6/2012 | Clarke et al. |
| 8,751,039 | B1 * | 6/2014 | Macoviak ............. A61J 7/0076 700/244 |
| 10,675,222 | B2 * | 6/2020 | Hudson ................ A61J 7/0084 |
| 2010/0253476 | A1 * | 10/2010 | Poutiatine ............. A61J 7/0418 340/10.1 |
| 2012/0012606 | A1 | 1/2012 | Longley et al. |
| 2015/0034667 | A1 * | 2/2015 | Shimmerlik ............. G07F 9/00 221/90 |
| 2015/0148943 | A1 * | 5/2015 | Sullivan ................ A61J 7/0076 700/231 |
| 2015/0259110 | A1 * | 9/2015 | Blackburn .......... G07F 17/0092 222/1 |
| 2016/0196503 | A1 | 7/2016 | Guan et al. |
| 2016/0355322 | A1 | 12/2016 | Burton, Jr. et al. |
| 2016/0357940 | A1 * | 12/2016 | Carter ................... A61J 7/0409 |
| 2018/0113995 | A1 * | 4/2018 | Hall ....................... G16H 10/60 |
| 2018/0165421 | A1 * | 6/2018 | Hall ....................... G16H 40/67 |

OTHER PUBLICATIONS

International Preliminary Report on Patentability dated Mar. 17, 2020 for International Application No. PCT/US2018/050722, 20 pages.

* cited by examiner

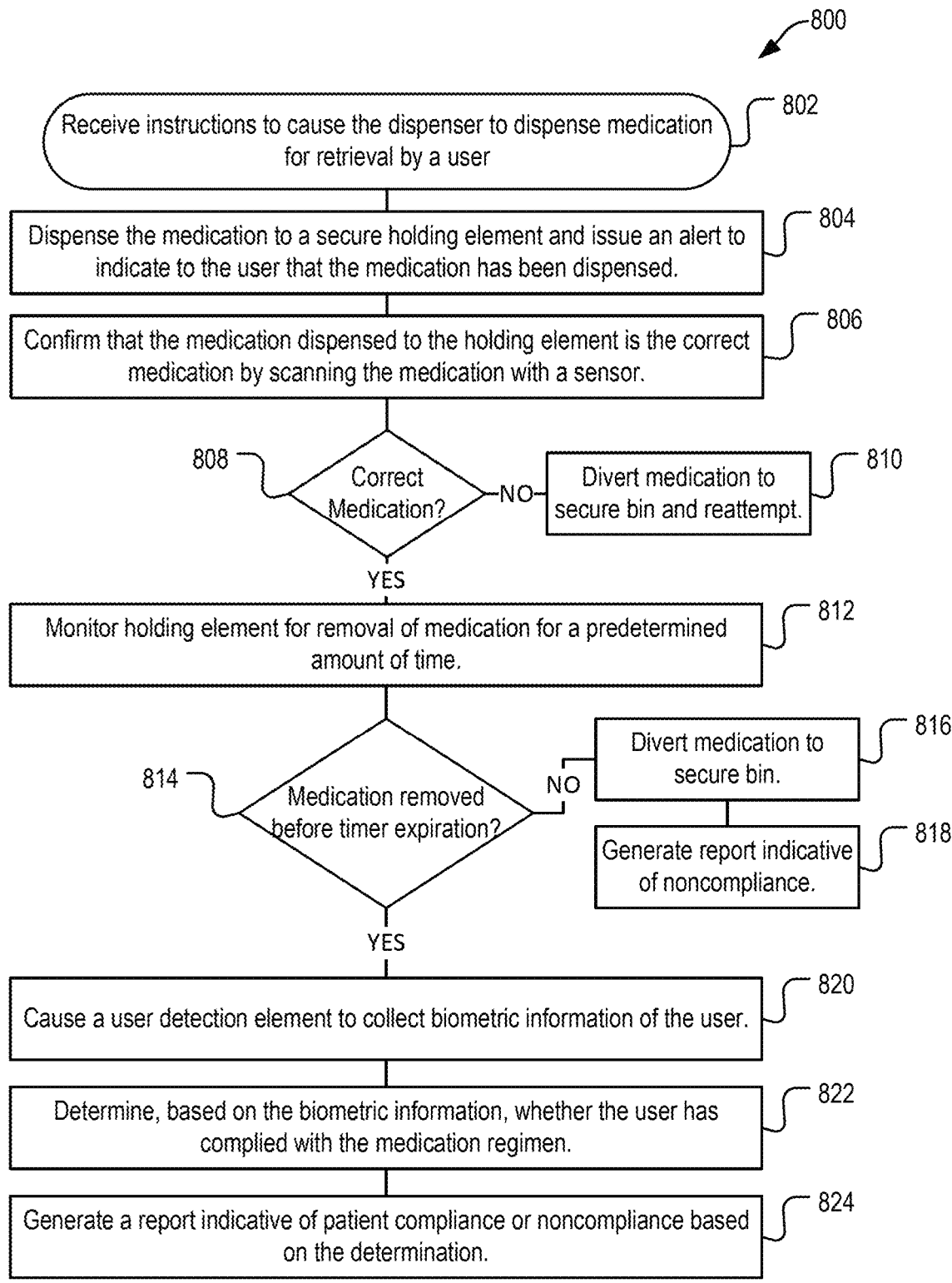

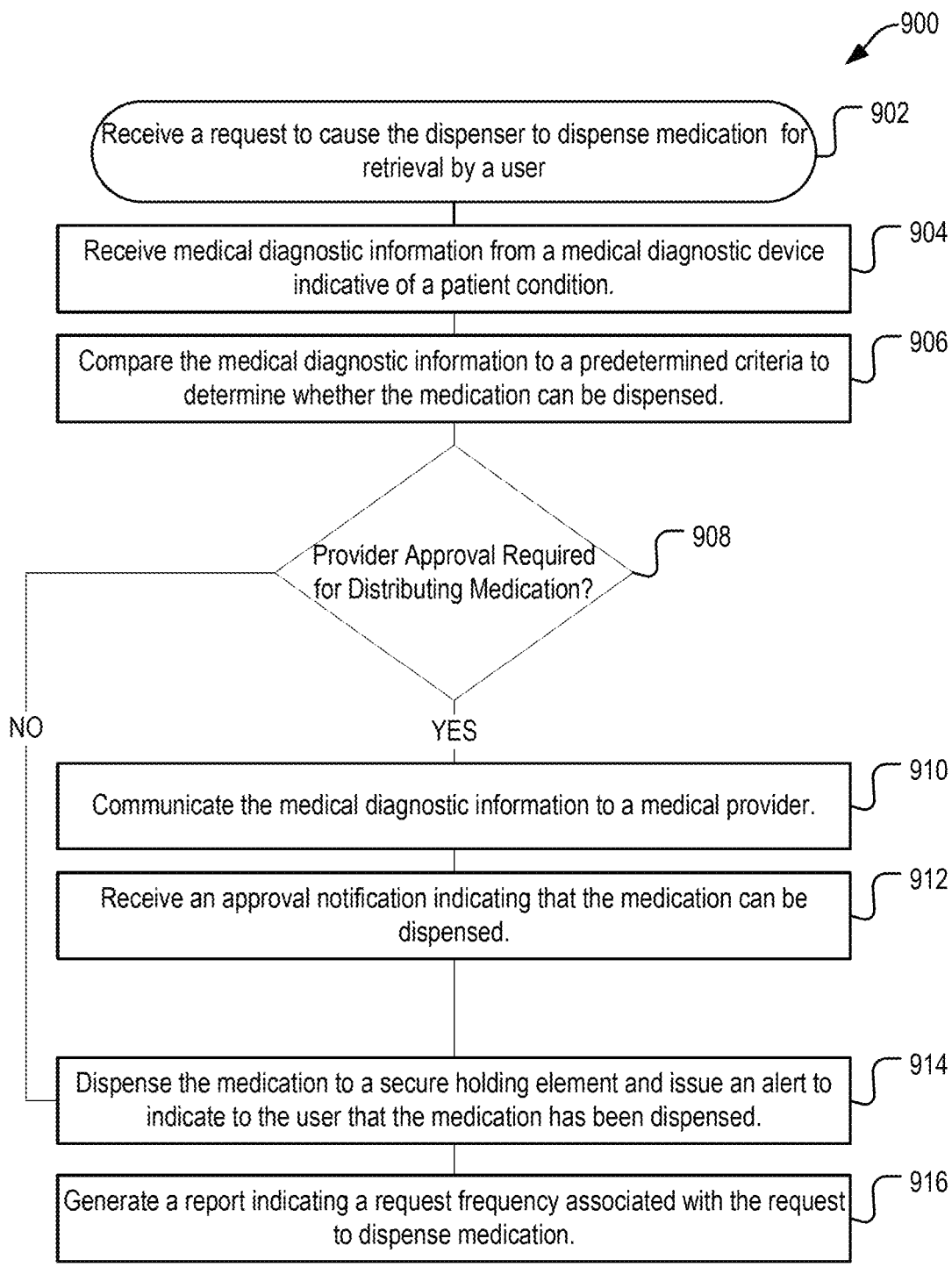

AUTOMATED AND SECURE METHODS FOR DISPENSING MEDICATION

CROSS REFERENCE TO RELATED APPLICATIONS

This application is a U.S. National Phase of International Application No. PCT/US2018/050722, filed Sep. 12, 2018, which is related to and claims priority benefits from U.S. Provisional Application Ser. No. 62/558,630 filed on Sep. 14, 2017, entitled "Automated And Secure Methods For Dispensing Medication", the disclosures of which are incorporated by reference herein.

TECHNICAL FIELD

Embodiments of the present application relate generally to a point of care device for integration into a patient's home or healthcare facility for facilitating the distribution of medication.

BACKGROUND

The healthcare industry is among the largest industries in the world, particularly in nations with aging populations. A critical component of this industry is the provision of at-home care, including the use of prescription medication as well as monitoring and patient-directed treatment of disease. Patient health outcomes often depend on the diligence with which individual patients monitor and procure their own at-home health care. However, the degree of treatment compliance can vary markedly depending on many factors, including patient-specific factors such as physical and mental health, willingness to undergo treatment, and ability to remember complex medication schedules or large numbers of medications. These factors tend to be exacerbated by advanced age, where the number of discrete medications may increase along with their potential side effects and interactions, while the patient's ability to remember their medication schedule may decrease. External factors can also influence patient compliance, such as the patient's ability to access healthcare facilities or to regularly obtain necessary medication from a pharmacy or doctor's office. Unfortunately, yet another critical consideration in the field of at-home health care is the possibility of misuse or misappropriation of potentially addictive or controlled medication, such as opioids.

Presently, most solutions for at-home medical care focus on tools to dispatch emergency responders to the home, or the provision of hands-on at-home care by a physician, nurse, or therapist. However, regular at-home care is expensive, time consuming, and can interfere with the privacy and daily life of the patient. Hands-off approaches, such as instructing the patient in the use of therapy or medication, are inappropriate for patients with difficulty remembering or complying with a medication regimen, or for patients who are potentially impacted by addiction. Regardless of the method by which medical care is provided, the possibility generally exists that controlled medication may be misappropriated whenever such substances are left under the sole control of a patient or patient's family, and not under direct control of the administering medical professional. And, in any event, patient compliance is generally difficult to monitor or enforce because, absent direct provider observation of the patient, compliance with a treatment or medication schedule is typically self-reported. Accordingly, there is a need for automation in the methods by which patients can be administered medication or medical treatment at home that provides for improved security against prescription theft, as well as methods that can improve patient compliance and patient health outcomes, that are not overly expensive or burdensome to the patient or medical providers.

BRIEF SUMMARY

At least one embodiment herein described relates generally to a point of care device for securely dispensing medication. The device can include an enclosure sized to contain a plurality of medication containers, a holding element accessible from outside the enclosure, wherein the holding element is positioned to receive medication containers from the enclosure, a dispenser configured to dispense medication from the enclosure to the holding element, a securable panel configured to provide access to the enclosure for retrieval or replenishment of the medication containers within the enclosure, a user detection element operable to detect biometric information of a user, and a computing device for controlling operation of the device. According to various embodiments, the enclosure can be configured to receive a cartridge containing the medication containers, the cartridge being preassembled to contain medication containers that meet the dispensing needs of a particular end user. The medication containers can include hard-sided containers or, in some cases, single-dose or multi-dose sachets, i.e. soft-sided plastic pouches containing one or multiple medications inside.

In accordance with various embodiments, the computing device can cause the dispenser to dispense a medication container from among the plurality of medication containers to the holding element. The device can then cause the user detection element to collect the biometric information of the user and determine whether the user is authorized or unauthorized to access the medication based on the biometric information. The device can generate an alert based on whether the user is authorized or unauthorized.

According to some embodiments, a point of care device for securely dispensing medication can detect, using a holding element sensor, whether a medication container has been removed from a holding element in order to detect whether a patient is complying with a medication regimen. If the point of care device continues to detect a medication container in the holding element after a predetermined period of time has elapsed, the point of care device can generate an alert indicative of user noncompliance. According to some specific embodiments, the system can determine based on user biometric data whether the user has complied with a medication regimen.

According to some embodiments, a point of care device for securely dispensing medication can detect biometric information of a user, determine, based on the user biometric information, whether the user qualifies for receipt of the medication; and cause the dispenser to dispense the medication container from among the plurality of medication containers to the holding element based in part on the user qualifying for receipt of the medication. According to specific embodiments, qualifying the user for receipt of the medication can include communicating patient biometric information to a medical provider and subsequently receiving clearance from the provider.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

The present disclosure will be better understood in view of the appended non-limiting figures, in which:

FIG. 8 is a process flow diagram illustrating a process for facilitating patient compliance at a POC device;

FIG. 9 is a process flow diagram illustrating a process for facilitating physician-directed or patient-directed medication dispensation and communication of patient medical information by a POC device.

DETAILED DESCRIPTION

Figure 1:
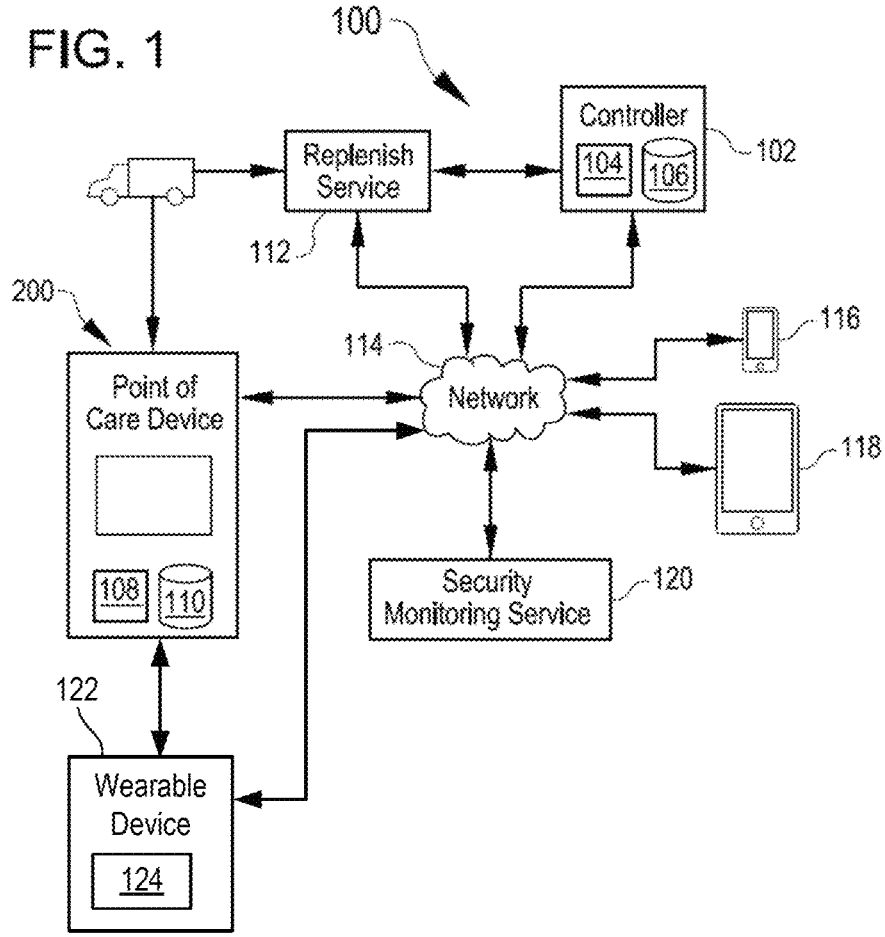
FIG. 1 is a simplified block diagram illustrating an example system incorporating a point of care (POC) device, in accordance with certain embodiments of the present disclosure.

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the invention. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

Embodiments of the present application relate generally to a point of care device (POC device) for integration into a patient's home or healthcare facility for facilitating the distribution of medication, which may be controlled or prescription medication, in a manner that is safe, secure, and encourages or monitors patient compliance with a medication regime. In specific embodiments, the POC device can be an in-home point of care device, i.e. one that is integrated into a patient's home, and which is capable of interacting with the patient to facilitate the distribution of medication. Exemplary POC devices can include some or all of the following features, including but not limited to, a hardware device for distributing medication, audio and/or visual detection devices for detecting patient speech, detecting patient biometric data, or enabling communication between a patient and healthcare provider via the POC device, artificial intelligence (AI) software and hardware (e.g. embedded AI analysis utilizing a chipboard, potentially in combination with centralized analysis via cloud connectivity), and cloud connectivity for connecting the patient (via the POC device) with multiple stakeholders such as supervisors or family members, medical providers, and the like.

Some embodiments include a system including the POC device as described above, in which the POC device is connected via a network with at least one medical provider. In some cases, the POC device is then operable to communicate with the healthcare provider when a condition has been met at the POC device. For example, the POC device may communicate with a pharmacy provider to indicate when a supply of medication has been depleted below a predetermined threshold, in order to request that the provider refill the prescription. The POC device may also be operable to generate a request to a medical provider to issue instructions to the POC device related to dispensing of medication, e.g., to allow the POC device to dispense additional quantities of controlled medications (e.g., pain medication such as opioids or the like) on demand by a patient in conjunction with approval by or notification of a medical provider.

By way of another example, the POC device may communicate with a security provider to indicate when tampering or unauthorized access has occurred at the POC device. In some cases, the POC device may use security features for detecting whether a user at the POC device is an authorized user or the holder of a prescription for medication to be dispensed. This determination can include some, all, or a combination of the following features: reading a secure code or password entered by the user at an input device, reading biometric information of a user by sensing physical attributes of the user, detecting unexpected or off-schedule access of the POC device, or detecting tampering with a lock or other secure alarm system of the POC device.

Turning now to the drawings, FIG. 1 illustrates an example system 100 incorporating a point of care (POC) device 200, in accordance with certain embodiments of the present disclosure. The system 100 can include a POC device 200 with onboard processing 108 and nonvolatile memory 110, which can contain instructions for facilitating various operations of the POC device, discussed in greater detail below with reference to FIGS. 2-3. The POC device 200 can include networking capabilities suitable for connecting the POC device with a network 114, e.g. a wired or wireless network, including but not limited to an internet-facilitated network, a local area network, or comparable, for communicating with various modules or services both inside and outside the home of a user.

In at least one embodiment of the present disclosure, the POC device 200 is operable to connect with a remote controller 102, e.g. a cloud-based or otherwise offsite computing system capable of directing operation of the POC device within the system 100. The controller 102 can include processing 104 and nonvolatile memory 106 for storing and executing instructions to aspects of the system 100. The controller 102 can also, in some cases, store information about the patient associated with a particular POC device 200, e.g., prescription information and contact information for connecting the patient with a medical provider, or with various services as described below. In some embodiments, the POC device 200 includes some or most of the operational instructions necessary to perform basic tasks, e.g. to maintain a medication schedule, present medication on time, monitor usage and compliance, and monitor tampering or misappropriation of medication. Embodiments of the POC device having such onboard functionality are advantageous when the POC device is intended to operate outside of the reach of reliable network connection. However, in alternative embodiments, the controller 102 may also be operable to control the POC device 200 and perform such processing tasks remotely. The controller 102 may also be operable to relay instructions from the POC device 200 to appropriate services.

According to some embodiments of the present disclosure, the POC device 200 is operable to connect, by the network 200, with a replenishment service 112 for accommodating regular refills of medication dispensed at the POC device, e.g. by initiating an order for a medication refill and generating instructions for the delivery of the refill at a medical provider. For example, the replenishment service 112 can be a software module operable to receive data communications from the POC device 200, such as requests for fulfillment of additional medication, indications that an existing prescription is running low or below a threshold, direct visual and/or audible communication from a patient at the POC device, and/or automated communications indicative that an existing prescription will need to be refilled. In some cases, the replenishment service 112 can be connected also to a medical provider, e.g. at a physical point associated with the replenishment service, such as the pharmacy, clinic, or doctor's office; or in some cases remotely via a computer or portable communication device of the medical provider (e.g. mobile device 116 or portable electronic device 118). In such cases, the replenishment service 112 can communicate with the medical provider prior to providing fulfillment of a medication to the POC device 200, e.g. to check the request against an existing medical record of approved medication, to request approval from a physician prior to facilitating delivery of a refill. Although potentially time consuming, this step can be used to maintain physician oversight of a course of treatment and prevent inadvertent overuse of prescription medication.

The POC device 200 may also be operable to connect, by the network 114, with a security monitoring service 120 that can receive alerts from the POC device regarding, e.g., tampering with medication stored therein, tampering with the dispensing mechanism of the POC device, or other attempts by unauthorized users to obtain medication from the POC device. The security monitoring service 120 can, upon detection of an alert, perform various actions. In some cases, the security monitoring service 120 can be configured to alert an administrator who determines whether the alert requires action. In some other cases, the security monitoring service 120 can be configured to issue instructions to the POC device not to distribute medication. The security monitoring service 120 can also, upon receiving an indication of tampering or medication theft, prepare and/or issue alerts to one or more devices, e.g. mobile device 116 and portable electronic device 118, or other suitable device connected with the network 114. In some cases, pushing notifications or alerts to such devices can include alerting a device of the patient (e.g., in the case that another person is removing medication), or alerting a device of a supervisor, caregiver, or medical provider. In some alternative embodiments, the POC device 112 can issue alerts to a mobile device 116 or portable electronic device 118 of the patient, for alerting the patient when a scheduled dose of a medication should be taken.

The POC device 200 may also, or alternatively, be operable to connect with one or more medical diagnostic tools, which can include wearable devices 124. In some embodiments, the wearable device 124 can also include a sensor 124 capable of detecting patient information, such as but not limited to: medical data (e.g., heart rate, blood pressure, activity level, insulin level), biometric data, or the like. Other diagnostic tools can include, e.g., a pulse oximeter, blood pressure cuff, weigh scale, blood glucose meter, etc. These devices could be connected with the POC device 200 by way of cables or connect wirelessly (e.g. via Bluetooth, ANT+, Zwave, or any other wireless protocol in the 2.4 Giga hertz range). In some embodiments, the POC device 200 and wearable device 122 may communicate via the network 114. In some other embodiments, the POC device 200 and wearable device 122 may communicate directly, e.g. over a local area network, a short-range network (e.g., Bluetooth, Zigbee, or the like), or over a wired connection. In such cases, the POC device 200 can be used as a relay for communicating information from the wearable device 124 to one or more services connected with the network 114.

Figure 2:
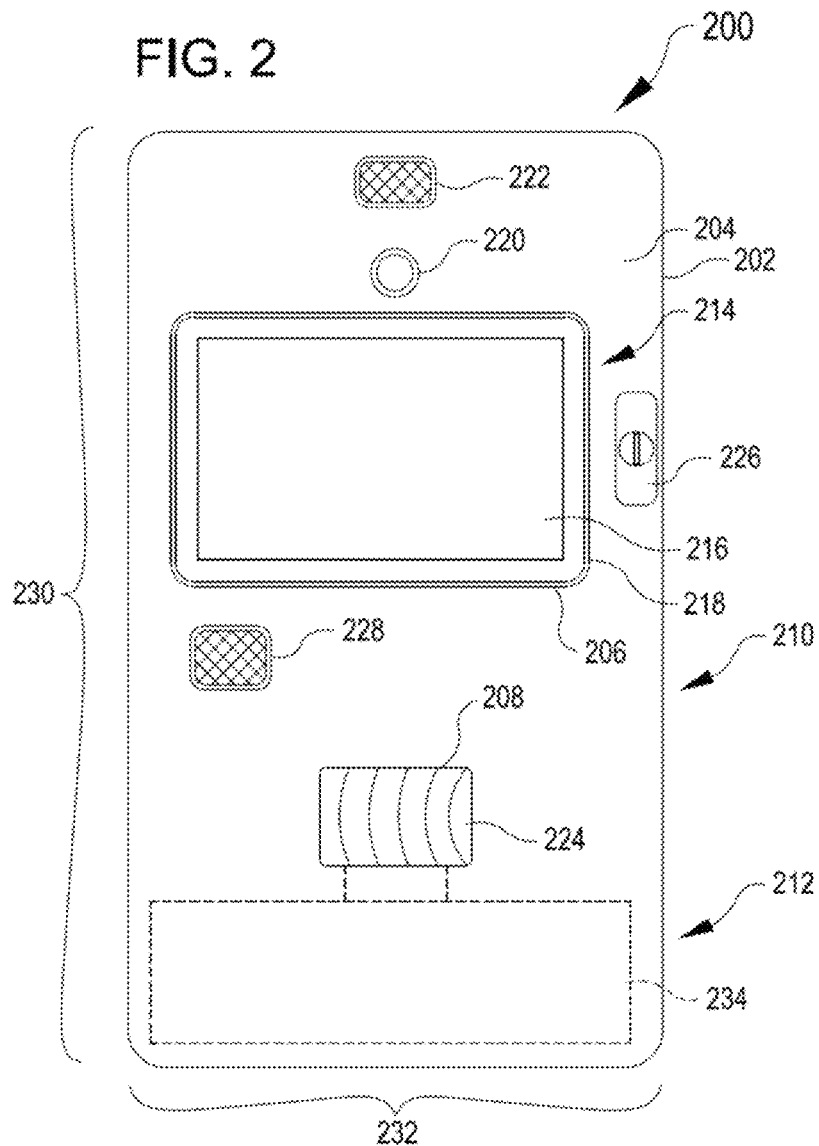
FIG. 2 is a front view of an example of a POC device for use in a system like that shown in FIG. 1 where the POC device is in a closed configuration, in accordance with at least one embodiment of the present disclosure.

FIG. 2 is a front view of an example of a POC device 200, which may be used as a standalone tool for automatically assisting patients with medication dispensation, compliance, and/or medication security, or which may be used in conjunction with a system like the system 100 shown in FIG. 1. The POC device 200 includes a frame 202 for containing a medication enclosure, with a front panel 204 attached thereto. In some cases, the front panel 204 can be attached to the frame 202 via a hinged connection for closing the enclosure and preventing or allowing entry. The front panel 204 can include a display opening 206 for presenting a display screen 216 of a display device 214 to a user, as well as a dispenser 208 for dispensing medication. Generally, the display device body 218 will be substantially contained behind the display opening 206 and is not removable therefrom through the display opening. In some embodiments, the display device 214 includes a touchscreen display screen 216 which can simultaneously communicate information to a user and receive inputs from the user. The frame 202 of the POC device 200 may be delineated into an upper portion 210 which contains the enclosure and medication therein, and a lower part 212 which is generally reserved for containing medication in a missed dosage container 234, where the medication has been declined or left in the dispenser 208 beyond a reasonable or predetermined duration.

The POC device 200 can include various sensors for receiving communications and/or for detecting biometric information from a user. For example, in one embodiment, the POC device 200 includes a camera 220, an audio output device or speaker 222, and an audio input device or microphone 228 for detecting patient movement and speech and/or for enabling two-way communication by the patient using the POC device. These sensors can be connected with the display device 214 and/or alternative computing resources (e.g. computing device 246, FIG. 3; or remote controller 102, FIG. 1) to analyze visual and/or audible information to perform such tasks as facilitating video conferencing between a user and a medical provider, matching visual and/or audible information (e.g., facial or voice recognition) with a known user to determine whether a user is authorized to access the POC device, and/or analyzing patient motion after taking medication to determine whether a patient is compliant with a course of treatment. The display device 214 can also include touchscreen capabilities, enabling password identification for determining whether a user is an authorized user.

The POC device 200 is generally configured to secure medication internally, making it inaccessible except to an authorized user at appropriate intervals, or to an authorized technician for periodically refilling medication and/or removing discarded medication. For example, the front panel 204 can be secured to the frame 202 by a locking element 226. The locking element 226 can be a mechanical lock, or in some cases an electrically actuated lock, which may be password-protected, accessible by way of recognition of the technician by biometric-based recognition protocol (e.g., facial recognition, voice recognition, fingerprint recognition, or other suitable recognition protocol), or which may be unlocked remotely in response to a valid request by the technician. In some embodiments, the locking element 226 may include a sensor that detects tampering or unauthorized entry and generates an alert for presentation to a user. The missed dosage container 234 is comparably secure, and is sized to accommodate a volume of discarded medication containers resulting from any missed doses. The security of the POC device 200 can be further enhanced by way of a shutter door 224 protecting the dispenser 208. In some embodiments, the shutter door 224 can be prevented from opening, e.g. by an internal actuator or locking feature (260, FIG. 3), which only opens when the POC device 200 has determined that the user of the POC device is an authorized user. For example, the POC device 200 may collect visual and audible information about a user via one or more sensors 220, 228, and then determine, e.g., via speech and/or facial recognition techniques, that the user is an authorized user, and subsequently open the shutter door 224. Conversely, if the POC device 200 determined that the user is an unauthorized user, the POC device could then cause the shutter door 224 to lock closed, and may additionally generate a message indicative of tampering or an unauthorized attempt at accessing medication, either for presentation to the intended user, to a supervisor or caregiver, or to a security service. Although the specific dimensions of the POC device can vary significantly depending on application, in some specific embodiments, the POC can be about 30 inches in height 230, about 12 inches in width 232, and about 4-6 inches in depth.

Figure 3:
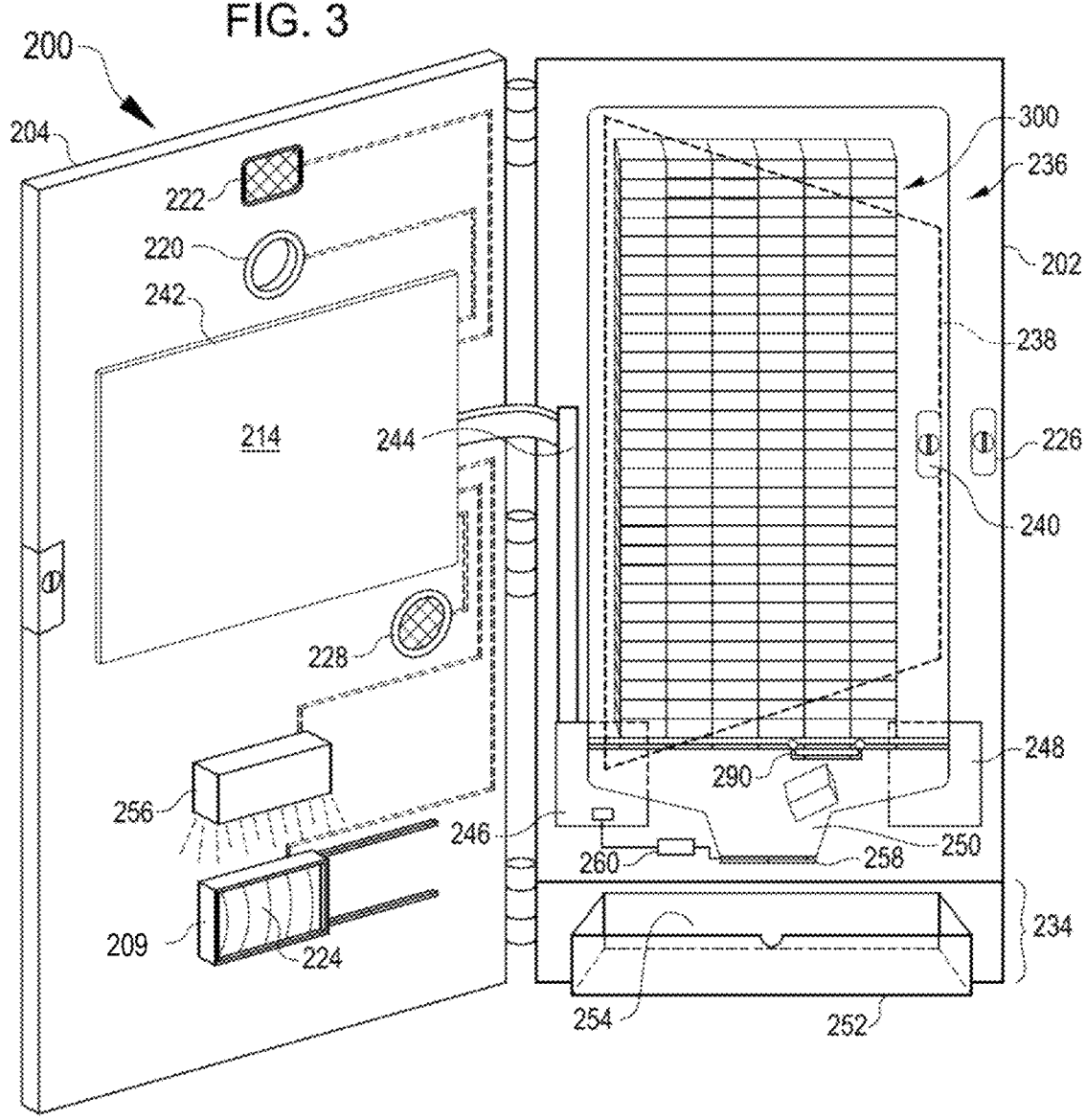
FIG. 3 is a front view of the POC device of FIG. 2 in an open configuration, with attention to internal components of the POC device.

FIG. 3 is a front view of the POC device 200 of FIG. 2 in an open configuration, with attention to internal components of the POC device 200. The front panel 204 is shown open, exposing the cartridge enclosure 236 and a contained cartridge 300 within the frame 202. The interior part of the front panel 204 can support various components of the POC device 200, including the display device 214, and the various sensors and communication equipment including camera 220, speakers 222, and microphone 228. An insulated panel 242 can further protect the display device 214, and can protect the interior of the POC device 200 from heating by the display device 214. The dispenser opening 208 and shutter door 224 are positioned in the front panel 204 beneath the display device 214, in proximity to a scanner 256 that is positioned to scan medication containers as they are released from the cartridge 300 and dispensed. According to some embodiments, the display device 214 and other components positioned within the front panel 204 may be operated by a computing device 246 located within the frame 202 of the POC device 200. In such cases, wiring for control and power supply for each of these components may be routed from the front panel 204 into the frame 202 by way of an insulating electrical wiring sleeve 244. In some embodiments, multiple mainboards (circuit boards) may be necessary for controlling operation of the components of the POC device 200, in which case the computing device 246 can be a primary mainboard and one or more secondary mainboards 248 may also be contained within the frame 202 and operably connected with the electronics therein.

Additional sensing elements may be incorporated into or operably connected with the interior electronic components (e.g., the primary mainboard 246 or secondary mainboard 248) of the POC device 200, such as but not limited to: condition sensors for detecting internal conditions of the enclosure (e.g. light level, temperature, humidity, etc.), and stock sensors or stock counters for detecting a quantity of medication containers remaining in the enclosure or a quantity that have been dispensed, tampering sensors such as accelerometers or the like for detecting attempts to remove or break the device, and other suitable sensors. For example, a condition sensor can monitor the internal environment of the enclosure on a continual or periodic basis, and generate an alert for a user when the internal environment exceeds a threshold condition such as a high temperature, high humidity, or high light level, any of which may damage stored medication. By way of another example, an accelerometer within the POC device can be used to detect shaking or other attempts to force entry into the enclosure 236, and provide an alert to a user, medical provider, or security service in response.

The frame 202 of the POC device 200 defines open internal spaces for the enclosure 236 that contains a cartridge 300 of medication containers, and for the missed dosage bin 234, which is positioned in a lower portion of the frame beneath the enclosure. The cartridge enclosure 236 can be secured by a shadow door 238 to prevent inadvertent release of cartridges. The shadow door 238 can extend and secure across the cartridge 300 in order to hold the cartridge in place when the front panel 204 is opened, allowing a technician access to the electronics independently of accessing the enclosure 238. The shadow door 238 may also be secured by way of a second locking element 240 which can be a snap lock, other mechanical lock, or an electrically actuated lock. In some cases, the shadow door 238 may be secured without locking.

The enclosure 236 empties into a presentation tray 250, which is accessible (and in some cases visible) through the dispenser opening 208. This presentation tray 250 can be fed medication containers from the cartridge 300 by a dispensing element 290, which is capable of selecting and mechanically dispensing medication containers from the cartridge 300. In some embodiments, the medication containers of a cartridge 300 are secured against a shelf or rail by the frame 202 and shadow door 238, which prevents the individual containers from falling into the presentation tray 250. In such cases, the dispensing element 290 includes an actuator that is movably mounted to a rail positioned at the base of the enclosure 236. The dispensing element 290 can control the actuator to push against individual medication containers from the cartridge 300 when installed in the enclosure. In some examples, the dispensing element 290 can cause the actuator to dispense a bottom-most medication container to fall. One of ordinary skill will appreciate that any other medication container can be intelligently dispensed by the dispensing element 290. For example, in some embodiments, the dispensing element 290 can be controlled to selectively eject a medication container from a particular column corresponding to a desired medication, e.g., in response to a patient, physician, or pharmacist request to dispense a particular medication; or in response to a programmed schedule that indicates the particular medication containers in that column.

Alternative constructions of the dispensing element 290 are possible without deviating from the spirit of this disclosure. For example, in some alternative embodiments, the dispensing element 290 supports the cartridge 300 (e.g., using a trap door mechanism, or other suitable mechanism), and selectively releases medication containers on demand, e.g. by opening at a position of a selected container.

The presentation tray 250 can include a similar mechanism, i.e. a trap door 258 controlled by an actuator 260, to temporarily support a medication container for retrieval by a user for a predetermined period of time, before opening the trap door to release the medication container into the missed dosage bin 234. The missed dosage bin 234 can include a pull-out catch tray 252 positioned in a tray cavity 254 for catching and retaining missed dosages.

The construction of the POC device 200 provides dual functionality: ease of use by a patient to take receipt of dispensed medication, in conjunction with compliance and authentication procedures detailed below; and rapid replenishment on demand by a pharmacy or delivery service. When the stock of medication containers contained in the cartridge 300 becomes depleted below a threshold, the POC device 200 can signal to a user that the stock is low, or can signal a medical provider or controller that the stock is low in order to automatically renew the cartridge. Then, either by way of a user or medical provider request, the POC device controller can approve delivery of a new cartridge. An approved delivery agent will receive an assembled cartridge from a pharmacy specialist containing the appropriate set of medication containers arrayed in the cartridge, and transport the cartridge to the site of the POC device 200. The POC device 200 can check a credential of the delivery agent, or can request approval from a medical provider or controller to provide access. Following validation of the delivery agent, the POC device can relay an authorization to access the interior of the device, and allow the delivery agent to access the front panel 204 and shadow door 236. The delivery agent can remove the old cartridge as a unit (or any remnant thereof) as well as any medication containers that had been previously deposited in the secure bin 234 into a secured transport case, and then insert the new cartridge into the enclosure 236, before closing the shadow door 236 and front panel 204. In some cases, the delivery agent may be authorized to gain access to the POC device 200 directly, e.g. using a key, key code, or other authentication method. However, generally, the delivery agent has to request access to perform the cartridge replacement by the controller or medical provider, as an added layer of security.

Figure 4:
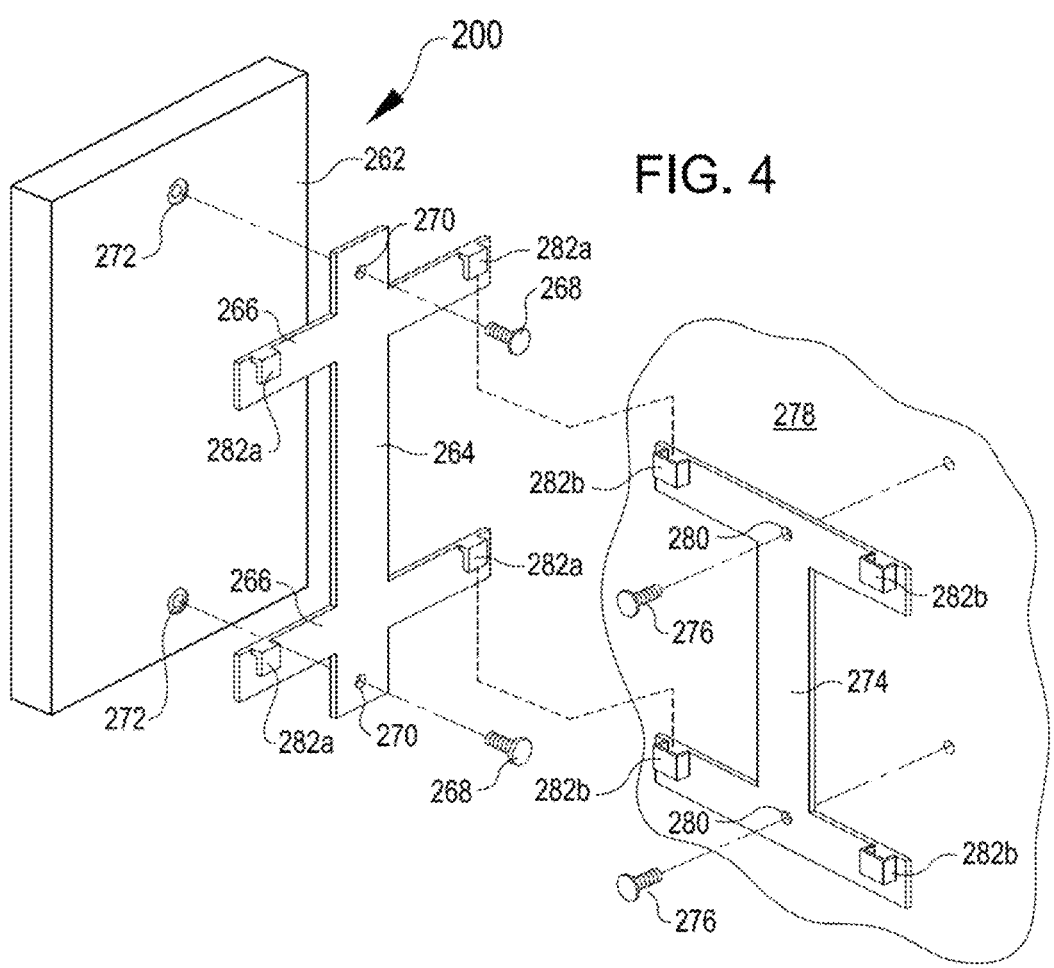
FIG. 4 is a back perspective view of the POC device of FIGS. 2-3 illustrating connecting features for attaching the POC device to a wall.

Embodiments of POC devices generally operate best when positioned to be readily accessible by the patient. To that end, the POC devices can be arranged to stand upright, e.g. on a table or countertop, or mounted to a wall at any suitable height. FIG. 4 is a back perspective view of the POC device 200 of FIGS. 2-3, and illustrates connecting features for attaching the POC device 200 to a wall, in accordance with some embodiments of the present disclosure. A first bracket 264 is connected with the back 262 of the POC device 200 via a set of mounting points 272, which can be threaded or unthreaded holes or the like. The first bracket 264 includes through-holes 270 for facilitating the connection of the first bracket to the POC device 200 by way of connectors 268 (e.g. bolts), cross-arms 266, and supporting hooks 282a positioned on the cross-arms. A second bracket 274 can be mounted to a wall 278 by way of connectors 276, such as screws or bolts, passed through a second set of through-holes 280. The second bracket includes a matching set of receiving elements 282b that connect with the supporting hooks 282a to connect the first and second brackets 264, 274 and support the POC device 200.

Figure 5:
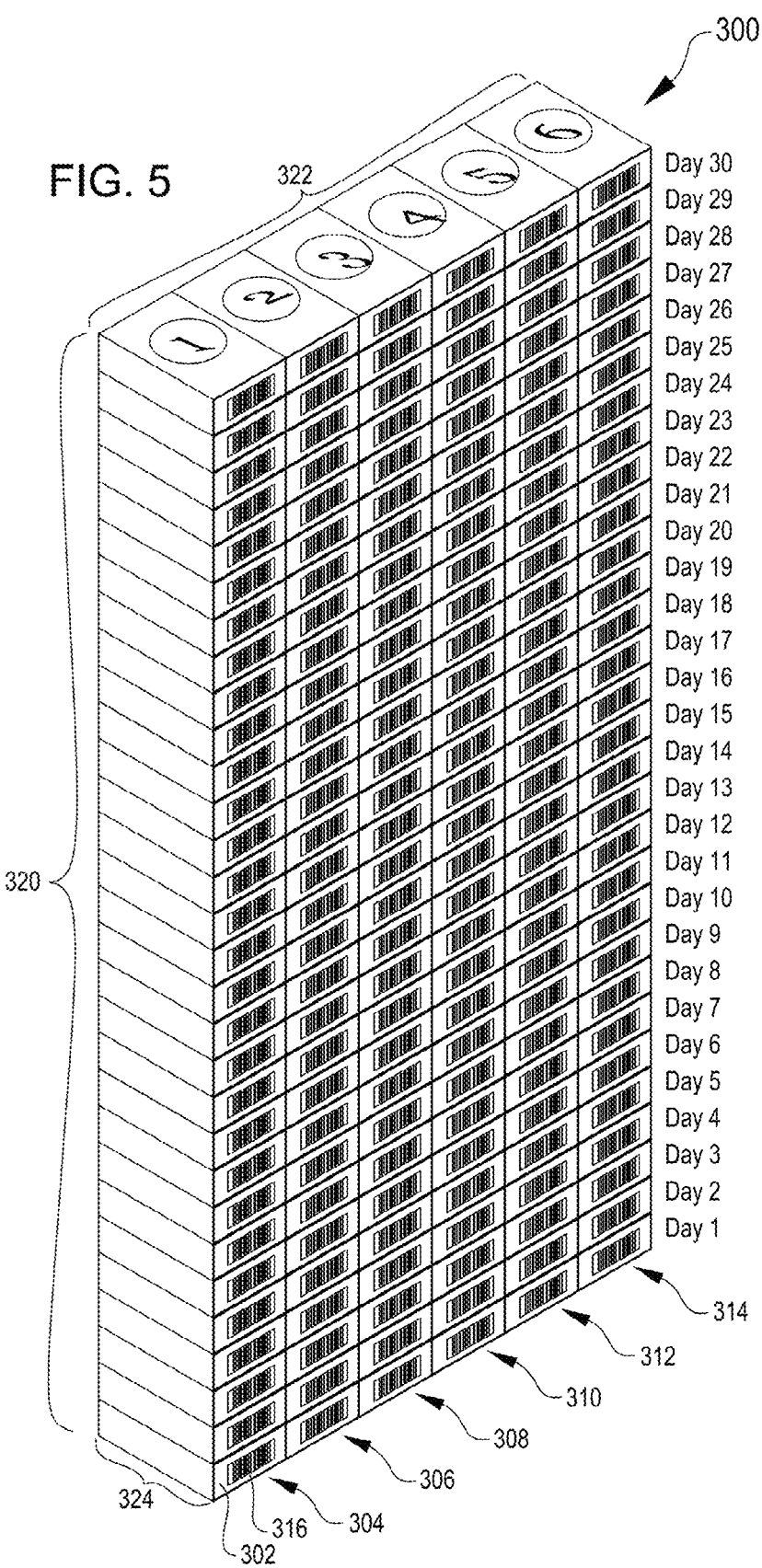
FIG. 5 is a perspective view of a medication container cartridge including multiple medication containers for insertion into a POC device like the POC device of FIGS. 2-4, in accordance with embodiments of the present disclosure.

FIG. 5 is a perspective view of a medication container cartridge 300 including multiple medication containers 302 for insertion into a POC device like the POC device 200 of FIGS. 2-4, in accordance with embodiments of the present disclosure. A cartridge 300 can be any suitable size that matches or is less than the interior dimensions of the enclosure 236. The medication container cartridge 300 generally has a depth 324 approximately equal to a depth of one medication container, which is approximately equal to a depth of the enclosure 236; but the containers in the cartridge can be stacked to a height 320 and width 322 capable of accommodating potentially many medication containers. In one example, a cartridge 300 can include about 30 rows of medication containers 302, and about six columns. In some embodiments, i.e. where a periodic medication regimen is simple and contains the same medications, the medication containers 302 may be interchangeable and can be dispensed in any sequence, e.g., all containers from a first column 304, then all containers from a second column 306, etc.

According to at least one embodiment, medication containers may be prepared for delivery based on different patient conditions. For example, medication containers may be delivered at different times, e.g. different pills for morning and evening, in which case the multiple columns 304-314 may be used for different groups of medications that correspond to different patient conditions, and the POC device 200 (FIGS. 2-4) can selectively release medication containers from the correct column given a particular time of day. By way of another example, different containers may be used to contain medication for use on a schedule as well as medication for use in symptom management. In some cases, one or more column may be reserved for on-demand medication, e.g. for pain management, even while other columns contain regular dosages for delivery on a schedule. In such cases, a first subset of the columns may be reserved for the regular dosages, while a second subset of the columns contains the on-demand medication.

Figure 6:
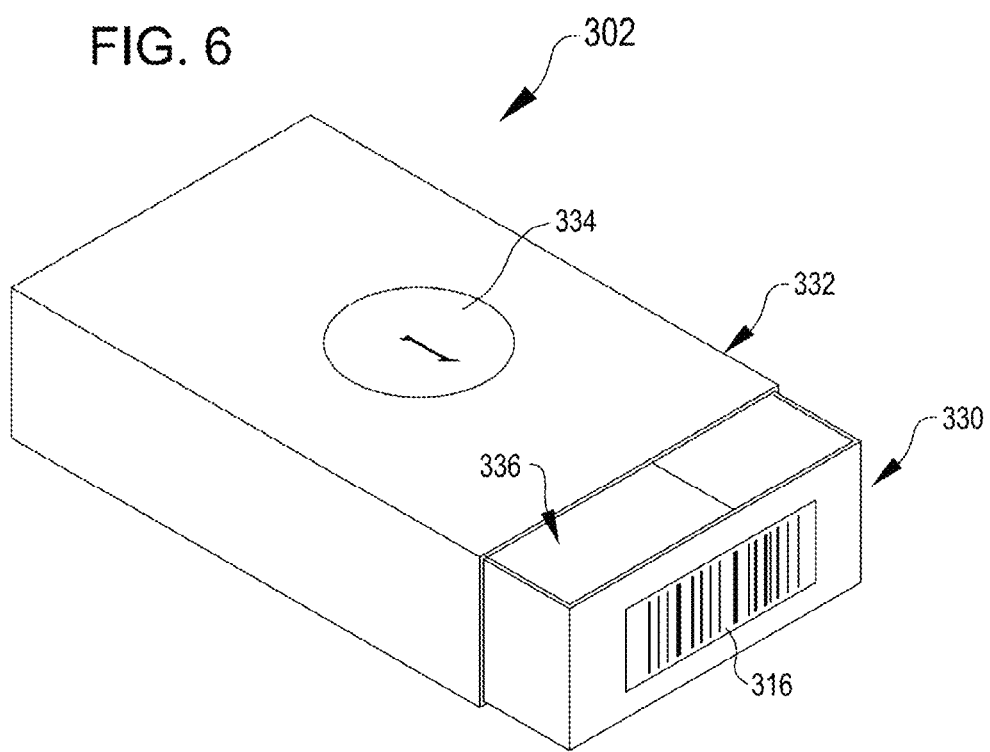
FIG. 6 is a perspective view of an individual medication container like those shown in the cartridge of FIG. 5 in a partially open configuration.

FIG. 6 is a perspective view of an individual medication container 302 like those shown in FIG. 5 in a partially open configuration. Each medication container 302 is a protective casing configured to retain, protect, and effectively label the medication contained therein. Each medication container 302 can include an inner tray 320 and an outer sleeve 332, or comparable feature, for protecting the medication inside and preventing spillage. The inner tray 330 defines a cavity 336 for containing the medication. The outer sleeve 332 and/or inner tray 330 can each include human and/or computer readable indicia to define what is contained in the medication container, and into which column the container should be placed to conform with a medication delivery schedule. For example, as shown, the medication container 302 includes a human-readable column indicia 334 stating which column the medication container is intended for; and a bar-code or comparable machine readable indicia 316 is visible at one end of the medication container to be read by a scanner when the medication container is released (e.g. scanner 256, FIG. 3). This final scanning step can be used to help ensure that the correct medication is always dispensed. The scanner can be an infrared scanner or optical scanner operable to detect machine-readable indicia on the medication containers, e.g. a barcode or QR-code reader, according to some embodiments, may be configured to read color-coded containers, or comparable alternatives. In some alternative embodiments, a secondary device, such as a portable electronic device, tablet, smartphone, or standalone scanner can be used to scan the medication container to confirm an identifier of the medication container and/or to confirm contents of the medication container. This feature may be used, e.g., in conjunction with certain pared-down embodiments of the point of care device 200 (FIGS. 1, 2) that lack an internal scanner; as a supplemental check for any embodiment of the point of care device; as a supplemental check for use by a user who is traveling away from a point of care device, or other comparable circumstances. This secondary confirmation may be communicated to a point of care device, e.g. by way of a local network or cable connection; or may be communicated wirelessly to a centralized controller, e.g., controller 102 (FIG. 1). Medication containers 302 as described above are generally arranged as a box-like enclosure, typically formed of a hard plastic, cardboard, or paper stock, but can take a variety of forms as described below.

According to some embodiments, medication containers 302 can also be implemented as single-dose or multi-dose sachets, i.e. soft-sided plastic pouches containing one or multiple medications inside. In some cases, multi-dose sachets can be preassembled with a set of medications selected and dosed for the intended user of the medication dispensing system. In some embodiments, sachets can be directly substituted for hard-sided containers in a cartridge, e.g. cartridge 300 (FIG. 5), and dispensed in the same manner as the hard-sided medication containers. Suitable modifications to a cartridge may be used to ensure accurate dispensing of a sachet, such as spring-loading a stack of sachets via a spring mechanism within each channel of the cartridge to prevent the sachets from becoming incorrectly oriented in the cartridge. Like hard-sided containers, sachets can include machine readable indicia capable of being scanned when the sachets are dispensed, so that affirmative confirmation of the correct medication and dose is achieved. In some embodiments, additional spacers or empty sachets may be loaded in the cartridge to support the sachets and prevent movement of sachets within a cartridge prior to the cartridge being loaded in a POC device.

FIGS. 7-10 illustrate example processes 700, 800, 900, 1000 for implementing secure medication dispensing in conjunction with a POC device like the POC device 200 of FIGS. 1-4, and particularly in the context of system for at-home care like the system 100 of FIG. 1. Some or all of the processes 700, 800, 900, 1000 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Figure 7:
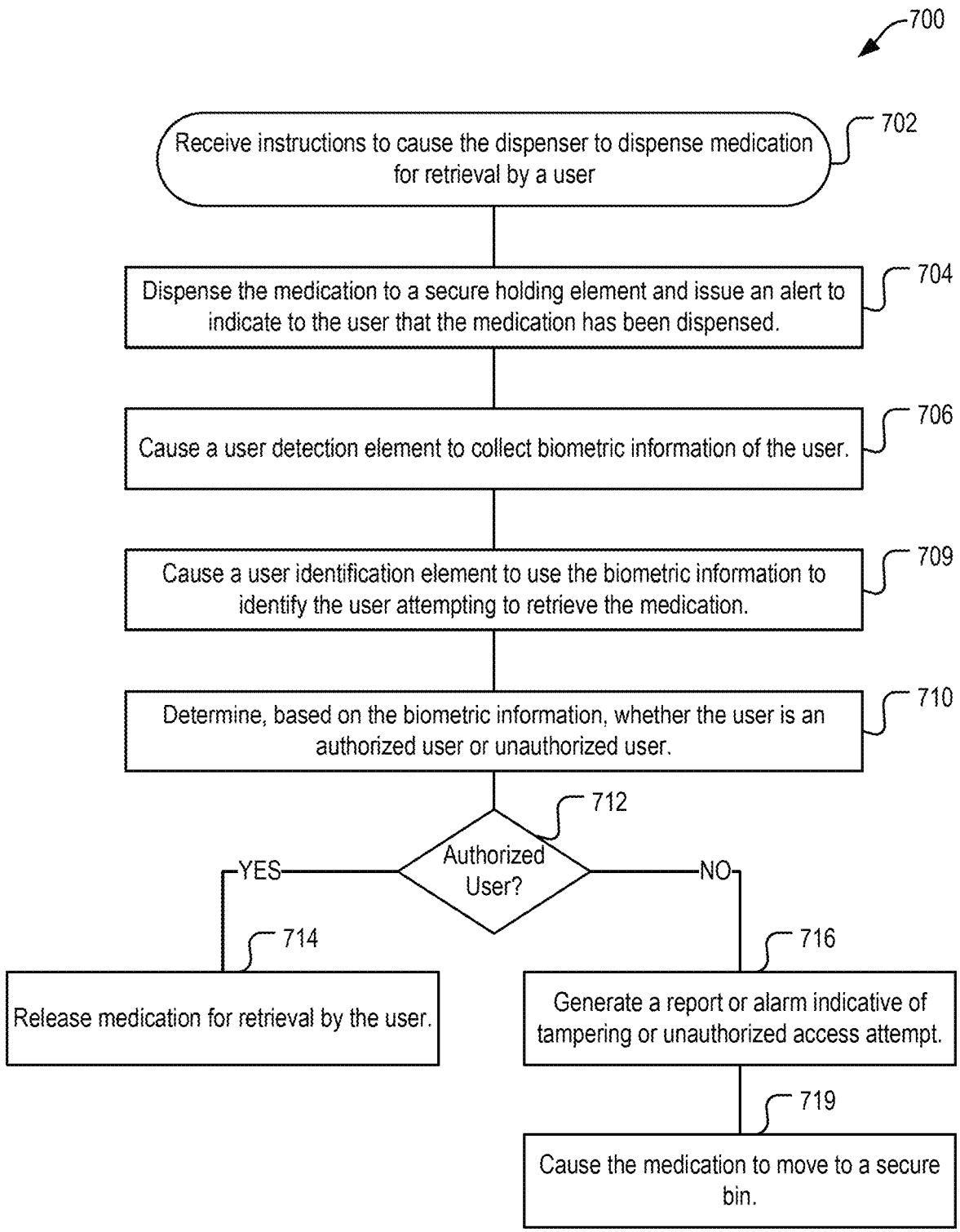
FIG. 7 is a process flow diagram illustrating a process for facilitating medication security at a POC device.

Techniques described herein include methods of implementing medication delivery via a POC device, particularly in the home. For example, FIG. 7 illustrates an example process 700 for securely distributing medication. Aspects of the process 700 may be performed, in some embodiments, by a similar system to the system 100 discussed with reference to FIG. 1, or by the processing components of a POC device as described in any of FIGS. 1-4. The system may also be implemented in conjunction with a distributed control architecture, i.e. an architecture in which various processing components are maintained across one or more, potentially many servers which may be offsite or cloud-based. In some embodiments, any suitable subset of the process steps of the process 700 may be performed in parallel except where expressly indicated otherwise.

In an embodiment, the process 700 includes receiving instructions to cause a dispenser to dispense a medication container from among a plurality of medication containers into a holding element for retrieval by a user (act 702). This instruction can be based on a timer in conjunction with a medication schedule, can be based on a command issued by a medical provider, or can be based on a patient request input at an input device associated with the POC device. In conjunction with receiving the instruction, the POC device can also issue an alert to indicate to the patient when the medication is to be dispensed (act 704). The system can then cause a user detection element, e.g. a camera, microphone, sensor or the like, to collect biometric information of the user (act 706). This biometric information can include, in some cases, directly identifying information such as a fingerprint; or can include a voice sample or image. The system can then use the biometric information to identify the user attempting to retrieve the medication (act 708). According to at least some embodiments, the medication containers can include multi-dose sachets that are pre-loaded with a set of medications tailored for the user. Multi-dose sachets can be dispensed in the same manner as the various forms of medication containers discussed above, or may be stored along a continuous roll and cut or otherwise removed from the roll prior to dispensing.

The user identification step can utilize various known AI techniques such as, but not limited to, machine learning algorithms suitable for training the system to identify users' faces, voice patterns, and other parameters. Suitable AI tools include OpenCV, Google Cloud Vision API, and Convolutional Neural Network machine learning models using the TENSORFLOW neural network AI available from Google, Inc. TENSORFLOW is an open-source software library for machine intelligence The process includes training the system to identify the users face and then in combination with the Vision API also will be able to identify the emotional state of the user, headwear and objects, along with the facial attributes. In particular, the process 700 can include determining, from user images, video, and/or speech captured by the POC device whether a particular user is an authorized or registered user of the POC device, or whether the user is an unauthorized user attempting to gain illicit access to the device (act 710). When the system has determined whether the user is an authorized or unauthorized user, the system can select different responses depending on whether the user is authorized or unauthorized (act 712). For example, the system can release the medication for retrieval by the user, e.g. by opening a shutter to allow access to a presentation tray containing the medication, if the user is authorized (act 714), or generate an alarm indicating that an unauthorized user has attempted to access the medication if the user is unauthorized (act 716). In this latter case, the system can also directly shunt the medication to a secure missed dosage bin (act 718).

According to various embodiments, a POC device can be used to facilitate patient compliance with a medication regime. This compliance monitoring can be performed in conjunction with medication security as described above with reference to FIG. 7, or can be performed separately. Therefore, unless explicitly stated otherwise, the process steps illustrated in the following figures can be performed either separately or in combination with one another.

FIG. 8 is a process flow diagram illustrating a process 800 for facilitating patient compliance with a medication regimen at a POC device, in accordance with at least one embodiment of the present disclosure. The process 800 includes receiving instructions to cause a dispenser to dispense a medication container from among a plurality of medication containers into a holding element for presentation to and retrieval by a user (act 802). This instruction can be based on a timer in conjunction with a medication schedule, can be based on a command issued by a medical provider, or can be based on a patient request input at an input device associated with the POC device.

In conjunction with receiving the instruction, the POC device can also issue an alert to indicate to the patient when the medication is to be dispensed (act 804). The system can perform a verification step to determine that the indicated medication or combination of medications has been dispensed, e.g., by scanning the dispensed medication with a sensor and verifying, based on an indicia on a medication container, that the correct medication has been dispensed (act 806). In some embodiments, this scanning step can be performed prior to dispensing the medication to the holding element. If an incorrect medication is dispensed (act 808), the system can divert the incorrect medication to a secure bin, and reattempt dispensing the medication (act 810). In some embodiments, the system can optionally generate a warning indicating the error in combination with, or instead of making a second attempt; or can generate a warning after two or more failed attempts have been made.

If the correct medication has been dispensed to the holding element (act 808), the system can proceed to monitor the holding element for a predetermined amount of time to determine whether the medication has been removed (act 812). Suitable methods for monitoring the holding element can include, e.g., detecting whether a presentation shutter enclosing the holding element has been moved by a mechanical or motion sensor, detecting the weight of the medication in the holding element by a force sensor, detecting motion within the holding element by an optical sensor, or other comparable method. In some embodiments, sensing whether the medication has been removed can be facilitated by emptying the contents of the holding element into the secure bin after a timer has elapsed, and detecting, e.g. by a sensor, whether a medication container falls into the secure bin. If the medication is not removed prior to the timer expiration (act 814), the system can divert the unused dose of medication to the secure bin (act 816) and generate a report indicative of noncompliance (act 818).

In some embodiments, the system can further determine whether a patient has complied with a medication regimen by observing, by way of biometric sensors (e.g., optical sensors, microphones, and the like), that the patient has actually taken the medication. To do so, the system first collected biometric information of the user, particularly image or video data (act 820). Then, using the image or video data, the system can determine whether the user has complied with the medication regimen (act 822). In some embodiments, the determination employs an adaptive AI algorithm (e.g., TENSORFLOW neural network AI available from Google, Inc.) in order to analyze the captured biometric data and assess whether the patient has actually complied with the medication regime (e.g., swallowed a pill, taken a shot, etc.). The AI algorithm can be trained by providing video data indicative of both compliance and noncompliance over time in a training protocol that iteratively amends the AI algorithm until the system can routinely detect both compliance and noncompliance. For example, according to some embodiments of the present disclosure, the AI algorithm can include a machine learning (ML) model that captures image frames and feeds training sets to the algorithm that represent action associated with medication compliance or noncompliance (e.g. swallowing a pill, discarding a pill, falsifying compliance, etc.). This ML model can be implemented in TENSORFLOW or comparable neural network AI. The ML model can be put into live production by using a serving system for machine learning models, such as but not limited to TensorFlow Serving (Google, Inc.), a high-performance ML model serving system designed for production environments. Additional machine learning services that can be used, e.g. to generate pre-trained models or generate tailored models, include Google Cloud AI (provided by Google, Inc.).

Once the system has determined whether the patient has complied with the medical regimen, the system can generate a report indicating whether the patient is compliant or noncompliant with the medication regimen (act 824). In some alternative embodiments, the system can also, or alternatively, send the image or video data and/or send any logged reports regarding patient compliance to a second party, such as a caretaker or medical provider, to verify compliance or noncompliance.

Generally, when the POC device provides an alert to indicate to a user that medication has been dispensed, the indication is provided across a broad alert system that can include, e.g., a visual alert from a device screen, audible alerts from a device speaker, text, phone, and email contact from linked software services, alone or in any suitable combination with one another.

In some embodiments, the system can determine whether to dispense medication as needed based on medical diagnostic information concerning a patient, e.g. measurable indicia of discomfort or symptoms, based on physician approval, based on a medication schedule determined for the patient, and/or based on other factors. FIG. 9 illustrates an example process 900 for issuing medication on demand based on medical diagnostic information. For example, in the process 900, the system can receive instructions to cause the dispenser to dispense medication, e.g. from a user or medical provider (act 902). The system can then receive medical diagnostic information, such as indicia of stress, heart rate, blood sugar, or other comparable measures indicative of a patient condition (act 904).

In some embodiments, the system can obtain the medical diagnostic information by capturing biometric information of the user by way of a sensor, such as an optical sensor, of the POC device as described above. However, the system may also employ a networked medical diagnostic tool or wearable device, e.g. wearable device 122 (FIG. 1), to collect diagnostic information. The medical diagnostic information can then be compared to a predetermined criteria set to determine whether the medication can be automatically dispensed. Alternatively, the system can determine that the indicated medication requires the approval of a medical provider (act 908), in which case the system can communicate the request and/or the medical diagnostic information to a medical provider (act 910) and wait to receive an approval notification indicative that the medication can be dispensed (act 912). Once approval is secured, or if no approval is required, the system can proceed to dispense the medication to a secure holding element for patient retrieval (act 914).

In alternative embodiments, the system may communicate a request to dispense medication to a responsible second party other than a physician (e.g., a nurse, a caregiver, a pharmacist, or other suitable medical personnel) prior to dispensing the medication. The system may optionally log any requests to dispense medication in order to provide a physician or caregiver with a record of the patient's behavior in seeking medication (act 916). Such logs can be particularly useful when the POC device is used to maintain potentially addictive medications such as opioids or the like, as early detection of addictive behaviors may be used to allow for early intervention.

The application has now been described in detail for the purposes of clarity and understanding. However, those skilled in the art will appreciate that certain changes and modifications may be practiced within the scope of the appended claims.

In the preceding description, for the purposes of explanation, numerous details have been set forth in order to provide an understanding of various embodiments of the present application. It will be apparent to one skilled in the art, however, that certain embodiments may be practiced without some of these details, or with additional details.

Having disclosed several embodiments, it will be recognized by those of skill in the art that various modifications, alternative constructions, and equivalents may be used without departing from the spirit of the embodiments. Additionally, a number of well-known processes and elements have not been described in order to avoid unnecessarily obscuring the present application. Accordingly, the above description should not be taken as limiting the scope of the present application or claims.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the present invention, subject to any specifically excluded limit in the stated range. Where the stated range includes one or both of the limits, ranges excluding either or both of those included limits are also included.

As used herein and in the appended claims, the singular forms "a", "an", and "the" include plural references unless the context clearly dictates otherwise. Also, the words "comprise," "comprising," "contains," "containing," "include," "including," and "includes," when used in this specification and in the following claims, are intended to specify the presence of stated features, integers, components, or steps, but they do not preclude the presence or addition of one or more other features, integers, components, steps, acts, or groups.

In the following, further examples are described to facilitate the understanding of the disclosure:

Example 1

A point of care device for securely dispensing medication, the device including: an enclosure sized to contain a plurality of medication containers; a holding element accessible from outside the enclosure, wherein the holding element is positioned to receive medication containers from the enclosure; a dispenser configured to dispense medication from the enclosure to the holding element; a securable panel configured to provide access to the enclosure for retrieval or replenishment of the medication containers within the enclosure; a user detection element operable to detect biometric information of a user; and a computing device including at least one processor and nonvolatile memory containing nontransitory instructions that cause the computing device to, at least: cause the dispenser to dispense a medication container from among the plurality of medication containers to the holding element; cause the user detection element to collect the biometric information of the user; determine, based on the biometric information, whether the user is authorized or unauthorized; and generate an alert based on whether the user is authorized or unauthorized.

Example 2

The point of care device of example 1, wherein: the plurality of containers includes two or more subsets of containers containing different medications; the dispenser is configured to selectively dispense medication containers from among the two or more subsets; and the computing device is further configured to: select the medication container from the plurality of medication containers based on a condition; and cause the dispenser to dispense the selected medication container.

Example 3

The point of care device of example 2, wherein the condition is indicative of a specific medication, and wherein the computing device is configured to determine the condition based on a medication schedule.

Example 4

The point of care device of any one of examples 2 or 3, wherein the condition is indicative of a specific medication, and wherein the computing device is configured to determine the condition based on a remote instruction from one of an administrator, doctor, or pharmacist.

Example 5

The point of care device of any one of examples 2-4, wherein the condition is indicative of a specific medication, and wherein the computing device is configured to determine the condition based on a user instruction including a request for the specific medication.

Example 6

The point of care device of any of the preceding examples, wherein the user detection element includes one or more of: a facial recognition device; a voice recognition device; or an input device configured to recognize a passcode.

Example 7

The point of care device of any of the preceding examples, wherein the computing device is further configured to generate a warning in response to detecting that the user is unauthorized.

Example 8

The point of care device of any of the preceding examples, further including a secure bin positioned to receive medication from the holding element; and wherein: the holding element further includes a presentation shutter and a trap door, wherein the presentation shutter provides access to the holding element for a user, and wherein the trap door is for transferring medication from the holding element to the secure bin.

Example 9

The point of care device of example 8, wherein the computing device is further configured to cause the holding element to open the presentation shutter when the user detection element detects an authorized user.

Example 10

The point of care device of any one of example 8 or 9, wherein the computing device is further configured to cause the holding element to secure the presentation shutter and open the trap door to transfer the medication to the secure bin when the user detection element detects an unauthorized user.

Example 11

The point of care device of any one of examples 8-10, further including a holding element sensor configured to detect medication in the holding element, wherein the computing device is further configured to cause the holding element to transfer the medication container to the secure bin by the trap door when the holding element sensor detects that the medication has not been removed from the holding element within a predetermined period of time.

Example 12

The point of care device of any of the preceding examples, further including a scanner configured to scan a machine readable code located on each medication container, wherein the computing device is further configured to detect, by the scanner, information associated with medication dispensed to the holding element.

Example 13

The point of care device of any of the preceding examples, wherein the user detection device is further configured to capture an image of the user, and wherein the computing device is further configured to: determine, based on the image, whether the user has complied with an instruction to consume the medication; and generate an alert indicative of user compliance based on the determining.

Example 14

The point of care device of any of the preceding examples, further including a condition sensor configured to record a condition corresponding to one or more of temperature, humidity, or light level in the point of care device; and wherein the computing device is further configured to: determine whether the condition exceeds a condition threshold; and generate an alert for presentation to the user when the condition exceeds the condition threshold.

Example 15

The point of care device of any of the preceding examples, wherein the computing device is further configured to: maintain a medication schedule; and cause the dispenser to dispense the medication container according to the medication schedule.

Example 16

The point of care device of any of the preceding examples, further including a communication device configured to communicate with a remote computing device to receive instructions.

Example 17

The point of care device of any of the preceding examples, further including a local networking device configured to communicate with a wearable diagnostic device to monitor a user status.

Example 18

The point of care device of example 17, wherein the computing device is further configured to: receive information concerning the user status by the local networking device; and cause the dispenser to dispense the medication container based in part on the user status.

Example 19

The point of care device of any of the preceding examples, further including a biometric sensor configured to detect biometric information of a user; wherein the computing device is further configured to: detect user biometric information of a user using biometric sensor; determine, based on the user biometric information, whether the user qualifies for receipt of the medication; and cause the dispenser to dispense the medication container from among the plurality of medication containers to the holding element based in part on the user qualifying for receipt of the medication.

Example 20

The point of care device of any of the preceding examples, wherein the medication containers are medication-containing sachets, preferably multi-dose sachets.

Example 21

A point of care device for securely dispensing medication, the device including: an enclosure sized to contain a plurality of medication containers; a holding element accessible from outside the enclosure, wherein the holding element is positioned to receive medication containers from the enclosure; a dispenser configured to dispense medication from the enclosure to the holding element; a holding element sensor positioned to detect medication in the holding element; a securable panel configured to provide access to the enclosure for retrieval or replenishment of the medication containers within the enclosure; a user detection element operable to detect biometric information of a user; and a computing device including at least one processor and nonvolatile memory containing nontransitory instructions that cause the computing device to, at least: cause the dispenser to dispense a medication container from among the plurality of medication containers to the holding element; detect, using a holding element sensor, whether the medication container has been removed from the holding element; and generate an alert based on whether the medication container has been removed, the alert being indicative of user compliance.

Example 22

The point of care device of example 21, further including a user detection element operable to detect biometric information of a user, wherein the computing device is further configured to: cause the user detection element to collect the biometric information of the user; determine, based on the biometric information, whether the user is authorized or unauthorized; and generate an alert based on whether the user is authorized or unauthorized.

Example 23

The point of care device of any of the preceding examples, wherein: the plurality of containers includes two or more subsets of containers containing different medications; the dispenser is configured to selectively dispense medication containers from among the two or more subsets; and the computing device is further configured to select the medication container from the plurality of medication containers based on a condition and cause the dispenser to dispense the selected medication container.

Example 24

The point of care device of example 23, wherein the condition is indicative of a specific medication, and wherein the computing device is configured to determine the condition based on a medication schedule.

Example 25

The point of care device of example 23, wherein the condition is indicative of a specific medication, and wherein the computing device is configured to determine the condition based on a remote instruction from one of an administrator, doctor, or pharmacist.

Example 26

The point of care device of example 23, wherein the condition is indicative of a specific medication, and wherein the computing device is configured to determine the condition based on a user instruction including a request for the specific medication.

Example 27

The point of care device of any of the preceding examples, wherein the user detection element includes one or more of: a facial recognition device; a voice recognition device; or an input device configured to recognize a passcode.

Example 28

The point of care device of any of the preceding examples, wherein the computing device is further configured to generate a warning in response to detecting that the user is unauthorized.

Example 29

The point of care device of any of the preceding examples, further including a secure bin positioned to receive medication from the holding element; and wherein: the holding element further includes a presentation shutter and a trap door, wherein the presentation shutter provides access to the holding element for a user, and wherein the trap door is for transferring medication from the holding element to the secure bin.

Example 30

The point of care device of example 29, wherein the computing device is further configured to cause the holding element to open the presentation shutter when the user detection element detects an authorized user.

Example 31

The point of care device of any one of examples 29 or 30, wherein the computing device is further configured to cause the holding element to secure the presentation shutter and open the trap door to transfer the medication to the secure bin when the user detection element detects an unauthorized user.

Example 32

The point of care device of any one of examples 29-31, wherein the computing device is further configured to transfer the medication container to the secure bin by the trap door when the medication has not been removed from the holding element within a predetermined period of time.

Example 33

The point of care device of any of the preceding examples, further including a scanner configured to scan a machine readable code located on each medication container, wherein the computing device is further configured to detect, by the scanner, information associated with the medication container when the medication container is positioned in the holding element.

Example 34

The point of care device of any of the preceding examples, further including a user monitoring device configured to capture an image of the user, wherein the computing device is further configured to: determine, based on the image, whether the user has complied with an instruction to consume the medication; and generate the alert indicative of user compliance for presentation to the user based on the determining that the user has taken the medication.

Example 35

The point of care device of any of the preceding examples, further including a condition sensor configured to record a condition corresponding to one or more of temperature, humidity, or light level in the point of care device; and wherein the computing device is further configured to: determine whether the condition exceeds a threshold; and generate an alert for presentation to the user when the condition exceeds the threshold.

Example 36

The point of care device of any of the preceding examples, wherein the computing device is further configured to: maintain a medication schedule; and cause the dispenser to dispense the medication container according to the medication schedule.

Example 37

The point of care device of any of the preceding examples, further including a communication device configured to communicate with a remote computing device to receive instructions.

Example 38

The point of care device of any of the preceding examples, further including a local networking device configured to communicate with a wearable diagnostic device to monitor a user status.

Example 39

The point of care device of example 38, wherein the computing device is further configured to: receive information concerning the user status by the local networking device; and cause the dispenser to dispense the medication container based in part on the user status.

Example 40

The point of care device of any of the preceding examples, further including a biometric sensor configured to detect biometric information of a user; wherein the computing device is further configured to: detect user biometric information of a user using biometric sensor; determine, based on the user biometric information, whether the user qualifies for receipt of the medication; and cause the dispenser to dispense the medication container from among the plurality of medication containers to the holding element based in part on the user qualifying for receipt of the medication.

Example 41

The point of care device of any of the preceding examples, wherein the medication containers are medication-containing sachets, preferably multi-dose sachets.

Example 42

A system for dispensing medication by a point of care device, the system including: a point of care device, including: an enclosure sized to contain a plurality of medication containers; a holding element accessible from outside the enclosure and positioned to receive medication containers from the enclosure; a dispenser contained in the enclosure and configured to dispense medication from the enclosure to the holding element; a securable panel configured to provide access to the enclosure for retrieval or replenishment of the medication containers within the enclosure; at least one sensing element configured to detect a condition associated with the point of care device; and an onboard computing device including at least one processor and nonvolatile memory containing nontransitory instructions that cause the onboard computing device to, at least: cause the dispenser to dispense a medication container from among the plurality of medication containers to the holding element, and generate data corresponding to the condition associated with the point of care device; and a medical diagnostic device including at least one sensor configured to detect biometric data of a user and a communication module operable to communicate the biometric data to the point of care device, wherein the instructions are further configured to, at least, cause the onboard computing device to collect the biometric data from the user by the at least one sensor.

Example 43

The system of example 42, wherein the instructions are further configured to cause the onboard computing device to: determine a user condition based on the collected biometric data; compare the user condition to predetermined criteria to determine whether the user condition meets the predetermined criteria; and cause the dispenser to dispense the medication based on the user condition meeting the predetermined criteria.

Example 44

The system of any of the preceding examples, wherein the instructions are further configured to cause the onboard computing device to communicate the biometric data to a medical provider.

Example 45

The system of example 44, wherein the instructions are further configured to cause the onboard computing device to: receive an approval notification indicating that the medication can be dispensed; and cause the dispenser to dispense the medication based on receiving the approval notification.

Example 46

The point of care device of any of the preceding examples, wherein the medication containers are medication-containing sachets, preferably multi-dose sachets.

Example 47

A point of care device for securely dispensing medication, the device including: an enclosure sized to contain a plurality of medication containers; a holding element accessible from outside the enclosure, wherein the holding element is positioned to receive medication containers from the enclosure; a dispenser configured to dispense medication from the enclosure to the holding element; a biometric sensor configured to detect biometric information of a user; a securable panel configured to provide access to the enclosure for retrieval or replenishment of the medication containers within the enclosure; a computing device including at least one processor and nonvolatile memory containing nontransitory instructions that cause the computing device to, at least: detect user biometric information of a user using biometric sensor; determine, based on the user biometric information, whether the user qualifies for receipt of the medication; and cause the dispenser to dispense the medication container from among the plurality of medication containers to the holding element based in part on the user qualifying for receipt of the medication.

Example 48

The device of example 47, wherein the biometric sensor includes a wearable device configured to communicate with the computing device by way of a wireless network.

Example 49

A system for managing the dispensing of medication, the system including: a point of care device, including: an enclosure sized to contain a plurality of medication containers; a holding element accessible from outside the enclosure and positioned to receive medication containers from the enclosure; a dispenser contained in the enclosure and configured to dispense medication from the enclosure to the holding element; a securable panel configured to provide access to the enclosure for retrieval or replenishment of the medication containers within the enclosure; at least one sensing element configured to detect a condition associated with the point of care device; and an onboard computing device including at least one processor and nonvolatile memory containing nontransitory instructions that cause the onboard computing device to, at least: cause the dispenser to dispense a medication container from among the plurality of medication containers to the holding element, and generate data corresponding to the condition associated with the point of care device; and a remote computing device including at least one processor and nonvolatile memory containing nontransitory instructions that cause the remote computing device to, at least: receive the data from the point of care device; and generate a warning for presentation to a remote user based on the data.

Example 50

The system of example 49, wherein the condition includes a quantity of the plurality of medication containers in the enclosure, and wherein the onboard computing device is configured to generate a request to replenish the point of care device in response to determining that the quantity of the plurality of medication containers in the enclosure is less than a threshold number of medication containers.

Example 51

The system of any one of examples 49 or 50, wherein the condition includes whether the medication container is present in the holding element, and wherein the onboard computing device is further configured to generate the warning in response to detecting that the medication container is present in the holding element for a duration of time exceeding a threshold duration of time.

Example 52

The system of any of the preceding examples, wherein: the point of care device further includes a user detection element operable to detect biometric information of a home user; the onboard computing device is further configured to cause the user detection element to collect the biometric information of the home user and determine, based on the biometric information, whether the home user is an authorized user.

Example 53

The system of example 52, wherein: the onboard computing device is further configured to communicate a warning to the remote computing device in response to determining that the home user is not an authorized user.

Example 54

The system of any of the preceding examples, wherein the onboard computing device is further configured to receive a medication schedule from the remote computing device and cause the dispenser to dispense the medication according to the medication schedule.

Example 55

The system of any of the preceding examples, wherein: the point of care device further includes a user interface operable to receive input from a home user; and the onboard computing device is further configured to generate a request to authorize dispensing of medication based on the input, receive an authorization from the remote computing device, and cause the dispenser to dispense the medication based on receiving the authorization.

Example 56

The system of any of the preceding examples, wherein: the onboard computing device is further configured to generate an alert for presentation to a home user in conjunction with causing the dispenser to dispense the medication container.

Example 57

The system of any of the preceding examples, further including: a remote client device configured to receive and send data; wherein the remote computing device is further configured to relay the warning to the remote user at the remote client device.

What is claimed is:

1. A system for dispensing medication, the system comprising:
   a medical diagnostic device comprising at least one sensor configured to collect biometric data of a user and a communication module operable to communicate the biometric data; and
   a point of care device configured to receive the biometric data from the medical diagnostic device, the point of care device comprising:
   an enclosure;
   a holding element connected with the enclosure, positioned to receive medication containers from the enclosure, and accessible from outside the enclosure;
   a dispenser connected with the enclosure and configured to dispense medication from the enclosure to the holding element;
   a securable panel that has an open configuration and a locked configuration, wherein the securable panel provides access to the enclosure for retrieval or replenishment of the medication containers in the open configuration and prevents access to the enclosure in the locked configuration; and
   a controller comprising at least one processor and non-volatile memory containing executable instructions that, when executed by the at least one processor, configure the controller to, at least:
   receive collected biometric data from the medical diagnostic device;
   determine, based on the biometric data, that the user is authorized to receive medication from the point of care device, wherein determining that the user is authorized to receive the medication comprises:
   determining, based on the collected biometric data, that the user has not exceeded a predetermined dosage or a predetermined frequency of accessing the medication, and
   at least one of:
   determining that an approval of a medical provider is required and receiving a notification indicating a required approval, and
   determining that an approval of a medical provider is not required; and
   cause the dispenser to dispense a medication container to the holding element in response to the determination that the user is authorized.

2. The system of claim 1, wherein the executable instructions, when executed by the at least one processor, further configure the controller to:
   determine a user condition based on the collected biometric data;
   compare the user condition to predetermined criteria to determine whether the user condition meets the predetermined criteria; and
   cause the dispenser to dispense the medication based on the user condition meeting the predetermined criteria.

3. The system of claim 1, wherein the executable instructions, when executed by the at least one processor, further configure the controller to:
   communicate the biometric data to the medical provider.

4. The system of claim 3, wherein the executable instructions, when executed by the at least one processor, further configure the controller to:
   receive an approval notification indicating that the medication can be dispensed; and
   cause the dispenser to dispense the medication based on receiving the approval notification.

5. The system of claim 1, wherein the medical diagnostic device comprises a wearable sensor configured to wirelessly communicate with the controller via a network.

6. The system of claim 1, wherein:
   the medical diagnostic device comprises a user interface operable to receive input from a home user; and
   the executable instructions, when executed by the at least one processor, further configure the controller to:
   generate a request to authorize dispensing of medication based on the received input;
   receive an authorization from a remote computing device; and
   cause the dispenser to dispense the medication based at least in part on receiving the authorization.

7. The system of claim 1, further comprising a remote client device configured to send and receive data, wherein the executable instructions, when executed by the at least one processor, further configure the controller to:
   generate an alert in response to receiving the collected biometric data; and
   relay the alert for presentation to a remote user via the remote client device.

8. The system of claim 1, wherein the executable instructions, when executed by the at least one processor, further configure the controller to:
   determine, based on the biometric data, that the user is not authorized to receive the medication; and
   prevent the dispenser from dispensing medication based on the determination that the user is not authorized.

9. The system of claim 8, further comprising a remote client device configured to send and receive data, wherein the executable instructions, when executed by the at least one processor, further configure the controller to:
   generate an alert in response to the determination that the user is not authorized;
   relay the alert for presentation to a remote user via the remote client device.

10. The system of claim 1, wherein:
determining that the user is authorized to receive the medication comprises determining, based on the collected biometric data, that the user has a qualifying medical condition or a qualifying diagnostic parameter.

11. A computer-implemented method of dispensing medication, comprising:
collecting biometric data of a user by a medical diagnostic device;
receiving the collected biometric information by a point of care device, the point of care device comprising:
an enclosure;
a holding element connected with the enclosure, positioned to receive medication containers from the enclosure, and accessible from outside the enclosure;
a dispenser connected with the enclosure and configured to dispense medication from the enclosure to the holding element; and
a securable panel that has an open configuration and a locked configuration, wherein the securable panel provides access to the enclosure for retrieval or replenishment of the medication containers in the open configuration and prevents access to the enclosure in the locked configuration;
determining, based on the collected biometric data, whether the user qualifies for receipt of medication from the point of care device, determining that the user is authorized to receive the medication comprises:
determining, based on the collected biometric data, that the user has not exceeded a predetermined dosage or a predetermined frequency of accessing the medication, and
at least one of:
determining that an approval of a medical provider is required and receiving a notification indicating a required approval, and
determining that an approval of a medical provider is not required; and
in response to a determination that the user qualifies, cause the dispenser to dispense a medication container to the holding element.

12. The computer-implemented method of claim 11, further comprising:
in response to a determination that the user does not qualify, prevent the dispenser from dispensing the medication container to the holding element.

13. The computer-implemented method of claim 12, further comprising:
in response to the determination that the user does not qualify, generate an alert for presentation to a remote user and communicate the alert to a remote client device.

14. The computer-implemented method of claim 11, wherein determining whether the user qualifies for receipt of the medication comprises:
comparing a parameter of the collected biometric data to predetermined medical diagnostic criteria; and
determining, based on the comparing, that the collected biometric data meets the predetermined medical diagnostic criteria.

15. The computer-implemented method of claim 11, wherein determining whether the user qualifies for receipt of the medication comprises:
communicating the collected biometric data to the medical provider; and
receiving an approval indication from the medical provider indicating that the user qualifies for receipt of the medication.

16. A point of care device for dispensing medication, comprising:
an enclosure sized to contain a plurality of medication containers;
a holding element connected with the enclosure, accessible from outside the enclosure, and configured to receive medication containers from the enclosure;
a dispenser connected with the enclosure and configured to dispense medication from the enclosure to the holding element;
a securable panel that has an open configuration and a locked configuration wherein the securable panel is provides access to the enclosure for retrieval or replenishment of the medication containers in the open configuration and prevents access to the enclosure in the locked configuration; and
a controller comprising at least one processor and non-volatile memory containing executable instructions that, when executed by the at least one processor, configure the controller to, at least:
receive diagnostic information comprising biometric data of a user;
determine, based on the diagnostic information, whether the user qualifies for receipt of the medication, determining that the user is authorized to receive the medication comprises:
determining, based on the collected biometric data, that the user has not exceeded a predetermined dosage or a predetermined frequency of accessing the medication, and
at least one of:
determining that an approval of a medical provider is required and receiving a notification indicating a required approval, and
determining that an approval of a medical provider is not required; and
cause the dispenser to dispense the medication container from among the plurality of medication containers to the holding element based in part on the user qualifying for receipt of the medication.

17. The point of care device of claim 16, further comprising a sensor configured to collect the biometric information from the user, wherein the executable instructions, when executed by the at least one processor, further configure the controller to:
generate the diagnostic information based on the collected biometric data from the sensor.

18. The point of care device of claim 16, further comprising a user interface operable to receive user input from the user, wherein the executable instructions, when executed by the at least one processor, further configure the controller to:
generate the diagnostic information based on the user input.

19. The point of care device of claim 16, further comprising a communication device configured to send and receive information via a network, wherein the executable instructions, when executed by the at least one processor, further configure the controller to:
relay the diagnostic information to at least one of the medical provider and a remote user via a client device in response to receiving the diagnostic information.

* * * * *